United States Patent
Kensey et al.

[11] Patent Number: 5,318,040
[45] Date of Patent: Jun. 7, 1994

[54] INSTRUMENTS AND METHODS FOR PERFORMING MEDICAL PROCEDURES VIA SMALL PERCUTANEOUS INCISIONS OR PUNCTURES WITHOUT USING A TROCAR

[75] Inventors: Kenneth Kensey, Chester Springs; John Nash, Downingtown; James J. Meikle, Jr., Broomall; Harold Clupper, West Chester, all of Pa.

[73] Assignee: Kensey Nash Corporation, Exton, Pa.

[21] Appl. No.: 936,419

[22] Filed: Aug. 27, 1992

[51] Int. Cl.5 ............................................. A61B 10/00
[52] U.S. Cl. ....................................... 128/754; 606/206
[58] Field of Search ........................ 128/749, 751-754; 606/205-208

[56] References Cited

U.S. PATENT DOCUMENTS

| | | | |
|---|---|---|---|
| 984,756 | 2/1911 | Frisch . | |
| 1,659,112 | 2/1928 | Littlejohn | 606/205 |
| 4,517,965 | 5/1985 | Ellison | 128/754 |
| 4,600,014 | 7/1986 | Beraha | 128/754 |
| 4,662,371 | 5/1987 | Whipple et al. | 604/22 |
| 4,667,684 | 5/1987 | Leigh | 128/754 |
| 4,681,123 | 7/1987 | Valtchev | 128/753 |
| 4,733,671 | 3/1988 | Mehl | 128/754 |
| 4,763,669 | 8/1988 | Jaeger | 128/751 |
| 4,872,456 | 10/1989 | Hasson . | |
| 4,877,026 | 10/1989 | de Laforcade . | |
| 4,881,551 | 11/1989 | Taylor | 128/754 |
| 4,907,599 | 3/1990 | Taylor | 128/754 |
| 4,917,100 | 4/1990 | Nottke | 128/749 |
| 4,924,878 | 5/1990 | Nottke | 128/751 |
| 4,953,558 | 9/1990 | Akerfeldt | 128/751 |
| 4,958,625 | 9/1990 | Bates et al. | 128/754 |
| 4,963,147 | 10/1990 | Agee et al. | 606/170 |
| 4,976,269 | 12/1990 | Mehl | 128/754 |
| 4,991,600 | 2/1991 | Taylor | 128/754 |
| 5,036,860 | 8/1991 | Leigh et al. | 128/754 |
| 5,048,538 | 9/1991 | Terwilliger et al. | 128/754 |
| 5,066,288 | 11/1991 | Deniega et al. | 604/274 |
| 5,080,655 | 1/1992 | Haaga | 128/754 |
| 5,133,724 | 7/1992 | Wilson et al. | 606/207 |

Primary Examiner—Max Hindenburg
Attorney, Agent, or Firm—Caesar, Rivise, Bernstein, Cohen & Pokotilow, Ltd.

[57] ABSTRACT

Apparatus and methods of use performing some medical procedure, e.g., positioning tissue, in the body of a being. The apparatus having a proximal portion and a distal portion, with the distal portion including a piercing end for forming a small percutaneous incision or puncture to enable the distal portion be inserted into the being's body to a desired internal position without the use of a trocar or other introducing device. The distal portion of the apparatus is elongated and has a longitudinal axis. An actuatable mechanism, e.g., a pair of moveable jaws, is located at the distal portion and is arranged to project outward laterally of the longitudinal axis for engagement with tissue located at the operative site to perform some operation, e.g., clamping. The actuatable mechanism is actuated by the proximal portion of the apparatus.

26 Claims, 6 Drawing Sheets

INSTRUMENTS AND METHODS FOR PERFORMING MEDICAL PROCEDURES VIA SMALL PERCUTANEOUS INCISIONS OR PUNCTURES WITHOUT USING A TROCAR

This invention relates generally to medical devices and methods of use, and more specifically to devices and methods of use for performing medical procedures within the body of a patient via a small percutaneous incision or puncture and without requiring the use of a trocar to provide access into the patient's body.

Various devices are commercially available for introduction, through a trocar into the body of a being to effect some laparoscopic or endoscopic procedure. One typical type of device comprises grasper for grasping and positioning, e.g., reflecting, tissue within the patient's body. Such devices comprise an elongated body member having a distal end at which a pair of pivotable jaws are located and a proximal, end at which a pair of pivotable actuating handles are located. The instrument is inserted within the patient's body through a conventional trocar until the pivotable jaws are located adjacent the tissue to be clamped. The actuating handles are then squeezed together to cause the jaws, which are coupled thereto, to grasp the tissue. Other types of trocar introduced devices used heretofore are staplers, biopsy devices, electrocautery devices, suturers, etc. The patent literature includes various devices for to effect some laporoscopic, endoscopic, or other minimally invasive procedure, e.g., U.S. Pat. Nos. 4,662,371 (Whipple et al.); 4,763,669 (Jaeger); 4,872,456 (Hasson); 4,917,100 (Nottke); and 4,963,147 (Agee et al.).

Other medical instruments utilizing jaws or cutting blades are shown in U.S. Pat. Nos.: 984,756 (Frisch); 1,659,112 (Littlejohn); and 4,877,026 (Laforcade).

While the prior art devices may be suitable for their intended purposes they never the less leave much to be desired from various standpoints. For example, instruments requiring the use of a trocar for percutaneous introduction typically require that the incision or puncture be sutured after the trocar has been removed. Obviously, this action is time consuming, relatively expensive, and wasteful of personnel resources. Moreover, the making of the incision or puncture sufficiently large for a conventional trocar is somewhat traumatic for the patient, particularly if multiple incisions or punctures are required to effect the percutaneous procedure.

Thus, the need exists for apparatus and methods for effecting medical procedures via very small percutaneous incisions or punctures, to expedite the procedure, conserve medical resources, minimize trauma to the patient.

OBJECTS OF THE INVENTION

Accordingly, it is a general object of this invention to provide apparatus and methods of accomplishing medical procedures by use of such apparatus through one or more small percutaneous incisions or punctures and which overcomes the disadvantages of the prior art.

It is a further object of this invention to provide apparatus and method of accomplishing medical procedures by use of such apparatus through one or more percutaneous incisions or punctures which are very small to minimize trauma to the patient.

It is a further object of this invention to provide apparatus and method of accomplishing medical procedures by use of such apparatus through one or more percutaneous incisions or punctures which are sufficiently small that they need not be sutured after the apparatus has been removed therefrom.

It is still a further object of this invention to provide apparatus and method of accomplishing medical procedures by use of such apparatus through one or more percutaneous incisions or punctures which are sufficiently small that they seal themselves after the apparatus has been removed therefrom.

SUMMARY OF THE INVENTION

These and other objects of this invention are achieved by providing apparatus and methods for performing some medical procedure in the body of a being. The apparatus has a proximal portion and a distal portion, with the distal portion comprising piercing means.

The piercing means is arranged for forming a small percutaneous incision or puncture in the body of the being to enable the distal portion of the apparatus to be inserted into the body of the being to a desired internal position without the use of a trocar or other introducing means.

The incision or puncture which is formed by the piercing means is sufficiently small that it is self-sealing after said distal portion of the apparatus has been removed from it.

The distal portion of the apparatus is elongated and has a longitudinal axis and additionally comprises first actuatable means arranged to project outward laterally of the longitudinal axis for engagement with tissue located at the desired position, e.g., operative site, to perform some operation on that tissue when said the first actuatable means is actuated.

In accordance with the teachings of this invention the first actuatable means may comprises any type of instrumentality to perform some procedure on internal tissue or internal structure( s ) . In the preferred embodiments shown and described herein that instrumentality comprises a pair of moveable jaws to enable one to clamp tissue therebetween for positioning that tissue. In one preferred embodiment the jaws are extendable from a retracted position to an extended position after the distal portion of the apparatus has been inserted through the incision or puncture to the desired internal position. In another preferred embodiment the jaws are already extended prior to insertion through the incision or puncture. The latter embodiment may, if desired, make use of a movable piercing tip. In particular, in accordance with other preferred embodiments of this invention the piercing tip may either be pivotable with respect to the distal portion of the apparatus in order to assume a retracted, e.g., safety, position after it has been used to form the percutaneous incision or puncture or may be removable from the distal portion of the apparatus after it has been used to form the percutaneous incision or puncture so that it can be located in a retracted, e.g., safety position.

BRIEF DESCRIPTION OF THE DRAWINGS

Other objects and many of the attendant advantages of this invention will readily be appreciated as the same becomes better understood by reference to the following detailed description when considered in connection with the accompanying drawings wherein.

DETAILED DESCRIPTION OF THE PREFERRED EMBODIMENT

Figure 1:
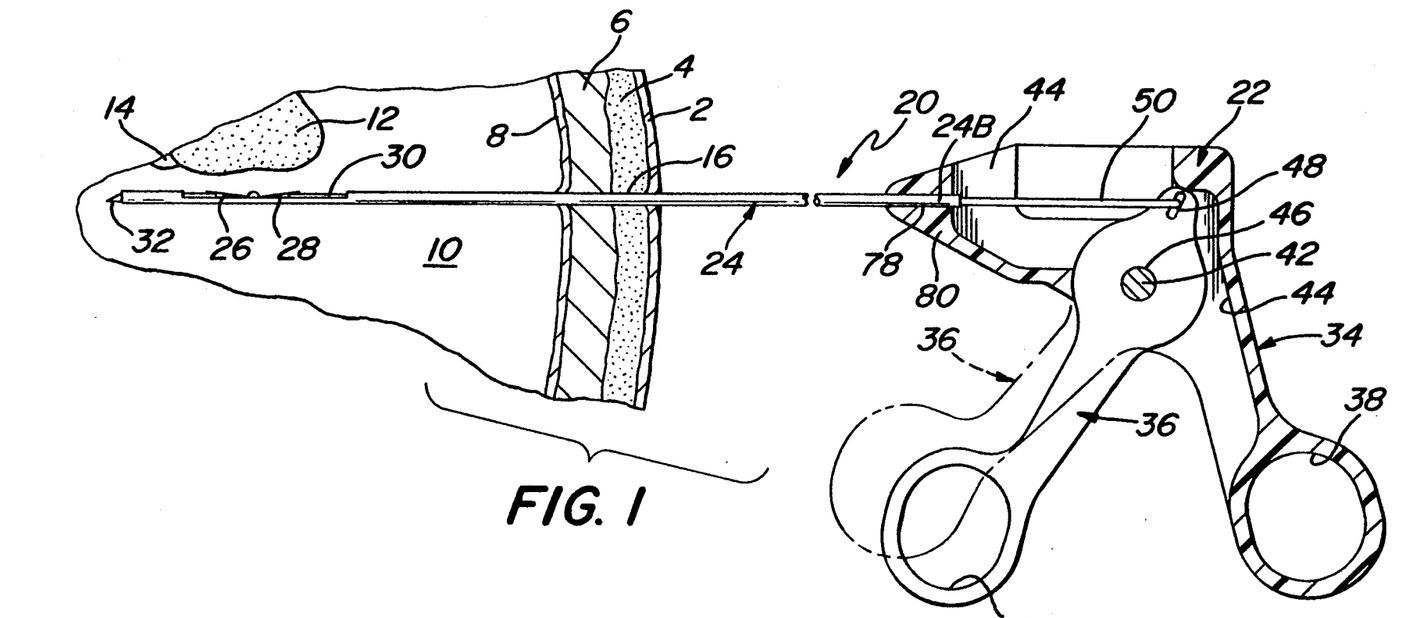
FIG. 1 is a side elevational view, partially in section, of one preferred embodiment of an instrument constructed in accordance with this invention shown after its piercing tip has formed a percutaneous puncture in the body of a patient so that the distal end portion of the instrument is located at a desired internal position.
Figures 6, 7:
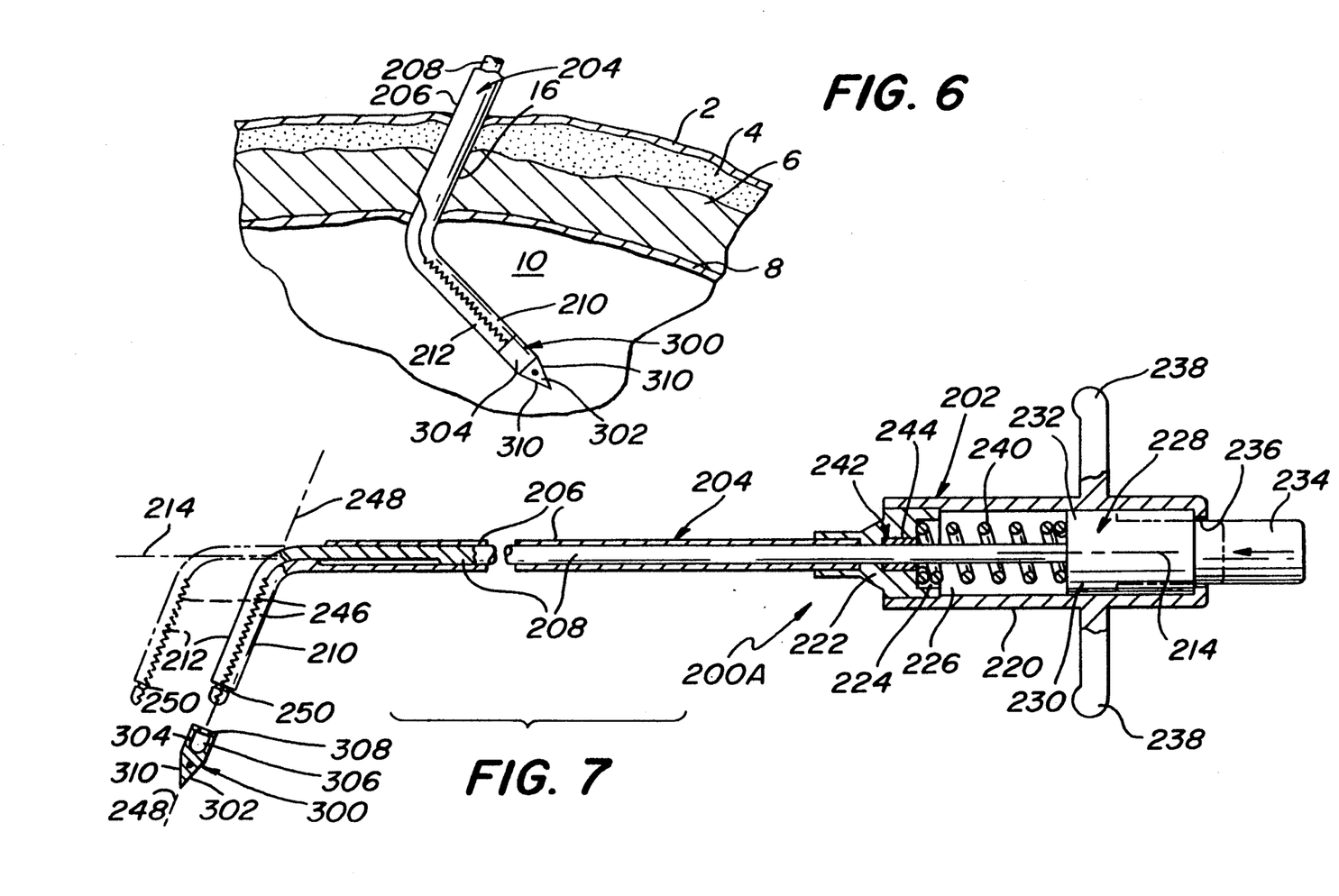
FIG. 6 is a side elevational view, partially in section, of the distal portion of a second preferred embodiment of an instrument of this invention shown with its piercing tip in position to effect its placement within the body of a patient.
FIG. 7 is an exploded side elevational view, partially in section, of the second preferred embodiment.
Figures 9, 10, 11:
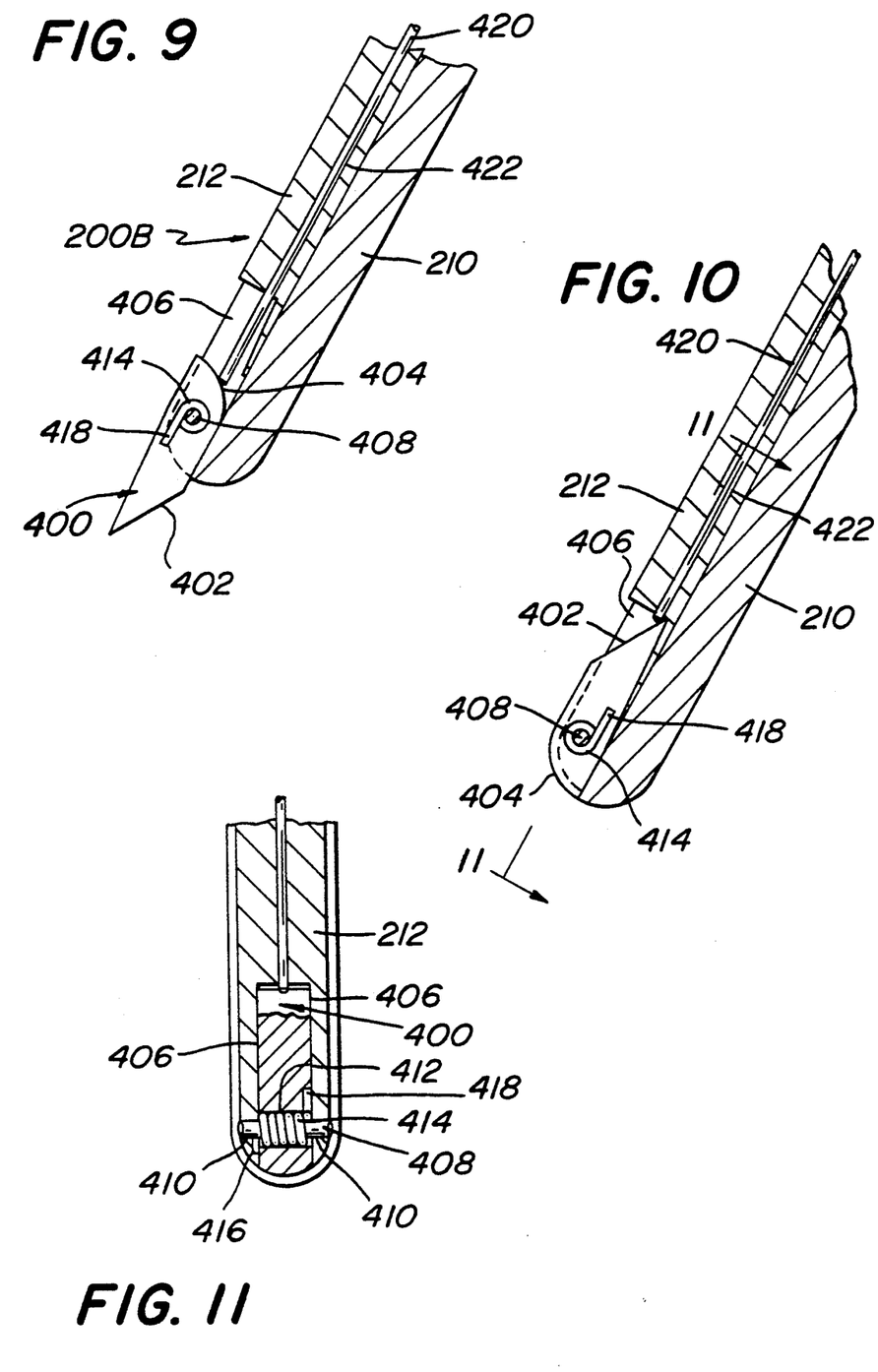
FIG. 9 is an enlarged longitudinal sectional view of the distal end of a third preferred embodiment of an instrument constructed in accordance with this invention and showing its piercing tip extended.
FIG. 10 is a view similar to FIG. 9 showing the third preferred embodiment of the instrument with its piercing tip retracted.
FIG. 11 is a sectional view taken along lines 11—11 of FIG. 10.

Referring now in greater detail to the various figures of the drawings wherein like reference characters refer to like parts there is shown in FIGS. 1, 7 and 9 respective embodiments 20, 200A and 200B of an instrument or device embodying the present invention. Each device 20, 200A and 200B is arranged to be extended, without use of any trocar or similar device, through the skin and underlying tissue of the body of a living being to perform some procedure therein, e.g., for grasping internal tissue to hold it in place or reflect it to a different position during endoscopic, laparoscopic, arthroscopic, or other similar percutaneous procedures.

In fact, each instrument is arranged to form the percutaneous incision or puncture, with the size of the percutaneous incision or puncture being sufficiently small that it seals itself upon removal of the instrument from it. To that end each instrument includes an elongated portion of very small diameter for forming the percutaneous incision or puncture and for passing therethrough into the body of the patient. The elongated portion includes a pair of members which extend (or are extendable) outward of the longitudinal axis of the elongated device (as will be described later) for grasping adjacent internal tissue, yet which do not interfere with the passage of the elongated portion of the instrument through the percutaneous incision or puncture to the operative situs.

It must be pointed out at this juncture that the instruments 20, 200A and 200B disclosed and described herein are merely exemplary of various types of instruments which can be constructed in accordance with the teachings of this invention. Thus, instruments can be constructed in accordance with the teachings of this invention for effecting other types of procedures, such as resecting, ablating, cauterizing, suturing, stapling, etc., which are desired to be carried out through a very small percutaneous incision or puncture to minimize patient trauma and to facilitate healing.

Referring now to FIGS. 1-5, it can be seen that the instrument 20 basically comprises a housing or body portion 22 from which an elongated tubular sleeve 24, formed of any suitable material, extends. The sleeve may be straight (as shown) or may be curved. In any case the distal end portion of the sleeve 24 includes means, e.g., a pair of jaws 26 and 28 (FIGS. 2 and 4), which are arranged to be extended laterally with respect to the longitudinal axis of the sleeve 24 out of a slot or window 30 so that they can be used to grasp internally located tissue. It should be pointed out at this juncture that the use of the term "axis" in this application is in the broadest possible sense and context, and, hence, is not limited to a straight line, but can be a line of any shape, e.g., a curved line, since the sleeve 24 need not be straight.

The instrument also includes a piercing tip 32, whose details will be described later. Suffice it for now to state that the piercing tip 32 includes a cutting edge at its distal end for piercing the patient's skin and underlying tissue to effect the percutaneous insertion of the sleeve of the instrument into the patient's body. In particular, the piercing tip 32 is arranged to extend out of the sleeve's distal end, which is open, so that it is in an extended position, like that shown in FIG. 1, whereupon its cutting edge is exposed. In that position the cutting edge can be used to pierce the skin and underlying tissue and the instrument's sleeve 24 slid therethrough to place its window 30 within the body of the patient, e.g., within his/her insufflated abdomen, adjacent the internally located tissue desired to be grasped, like shown in FIG. 1.

Figure 3:
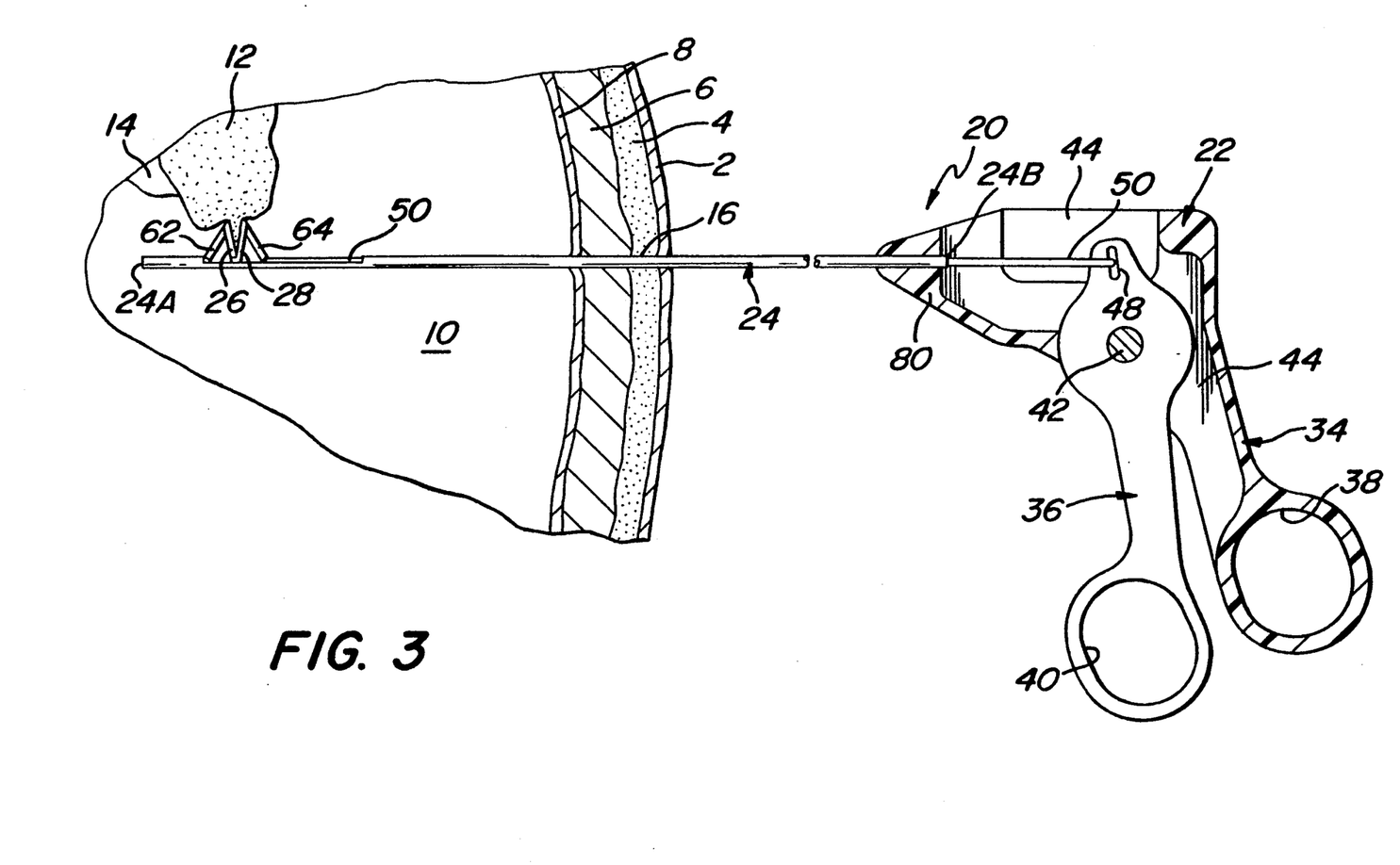
FIG. 3 is a side elevational view similar to FIG. 1 but showing the distal end of the instrument with its piercing tip retracted and its jaws extended laterally outward to grasp and reflect adjacent internal tissue.

The piercing tip is also arranged to be slid back through the open distal end of the sleeve into a retracted position, like that shown in FIG. 3, so that its cutting edge is no longer exposed, and hence cannot present any danger to adjacent internally located tissue. When the piercing tip is brought to the retracted position it is automatically locked in place therein. This action also readies the instrument to have its jaws 26 and 28 extended out of the window 30 to grasp the adjacent internally located tissue.

The means for effecting the foregoing operations of the instrument 20 comprise a pair of handle elements 34 and 36. These element form a portion of the instrument's body 22 and will be described in detail later.

In accordance with a preferred aspect of this invention the outside diameter of the sleeve 24 is very small, e.g., the sleeve is a 0.109 inch (2.77 mm), so that the formation of the percutaneous puncture is accomplished readily and relatively atraumatically. Moreover, by making such a small puncture the instrument 20 does not require the use of a trocar or other similar porting device to enable it to be extended through the puncture to the desired internal situs, thereby simplifying the insertion procedure. Further still, and quite significantly, since the instrument 20 forms a very small percutaneous incision or puncture there is no need to suture or otherwise artificially seal it after the instrument is removed. In fact, the incision or puncture is so small that it seals itself very quickly (almost immediately) after the instrument has be removed from it The handle element 34 basically comprises an elongated extension of a the body portion 22. The lower end of the handle element 34 has a thumb hole 38 at the free end thereof. The handle element 36 also comprises an elongated member, and it includes a finger hole 40 at the free end thereof. The handle element 36 is pivotally mounted onto the body portion 22 and serves as the operating "trigger" of the instrument 20. In particular, the trigger member 36 is pivotally mounted at its upper end to the upper portion of the handle element 34 where that element merges with the body portion 22. The means for effecting that pivotable connection comprises a pivot pin 42 projecting upward from the inside surface of a recess 44 in the body portion and contiguous handle element. The pivot pin 42 extends through a hole 46 in the upper end of the trigger handle 36.

Figure 2:
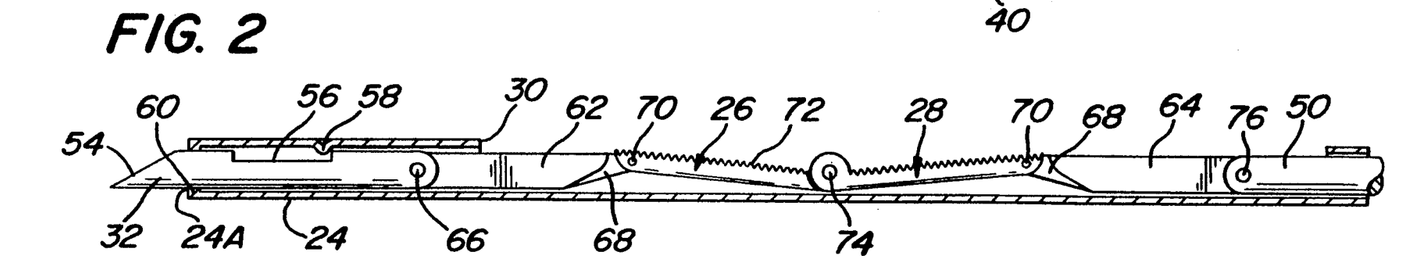
FIG. 2 is an enlarged longitudinal sectional view of the distal portion of the instrument shown in FIG. 1.
Figure 4:
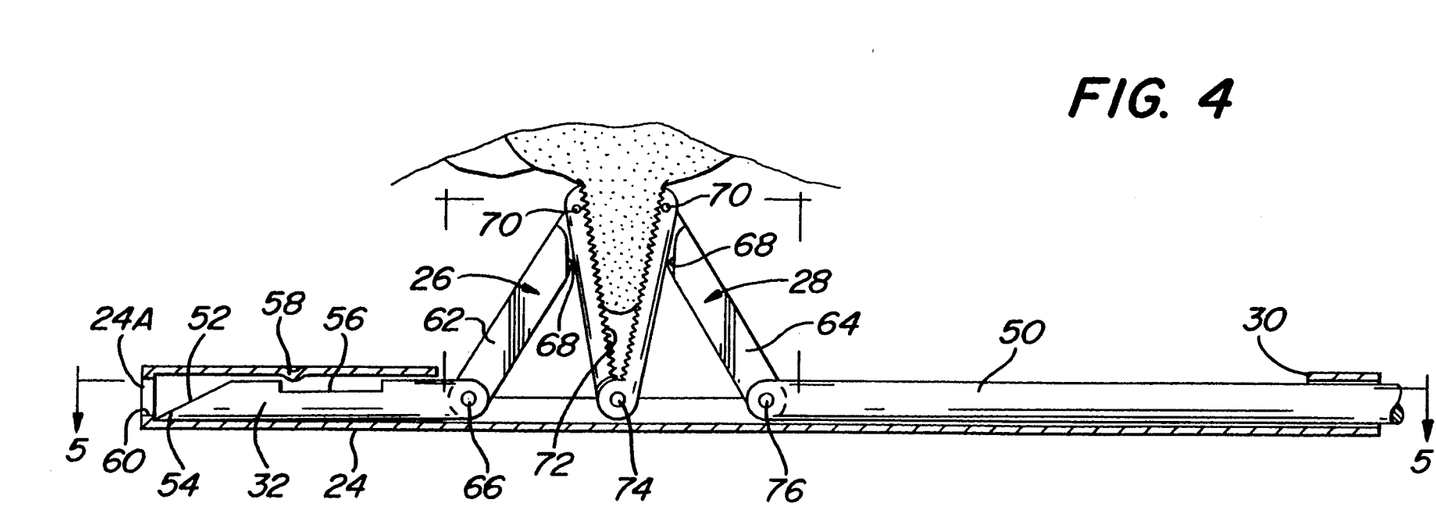
FIG. 4 is an enlarged longitudinal sectional view, similar to FIG. 2, but showing the jaws of the instrument clamping internal tissue therebetween.

The upper end of the trigger handle 36 includes a small extension in which a short slot 48 is located. The slot 48 serves as a means to receive a pin connected to the proximal end of an actuating rod 50. The actuating rod 50 is an elongated member which is disposed within the sleeve 24 and serves as the means for effecting the extension/retraction of the piercing tip 32 and for effecting the extension/retraction and operation of the clamping jaws when the trigger handle 36 is moved with respect to the handle element 34. Those operations will be described in detail later. Suffice it for now to state that the actuating rod 50 is arranged to be moved in the distal direction through the sleeve by the trigger handle 36 to position the tip 32 in the extended position as shown in FIGS. 1 and 2. It is also arranged to be moved in the proximal direction by the trigger through the sleeve to position the tip 32 in a retracted (locked) position before the jaws are extended out of the window 30. The rod 50 is also arranged to be moved in the distal direction through the sleeve by the trigger handle to effect the lateral extension of the jaws 26 and 28 out of the sleeve's window 30 and for moving the jaws toward each other to grasp adjacent tissue as shown in FIGS. 3 and 4. Lastly, the rod is arranged to be moved in the proximal direction through the sleeve by the trigger handle to move the jaws 26 and 28 apart to release the tissue and to retract the jaws back through the window 30 into the sleeve 24.

Figure 5:
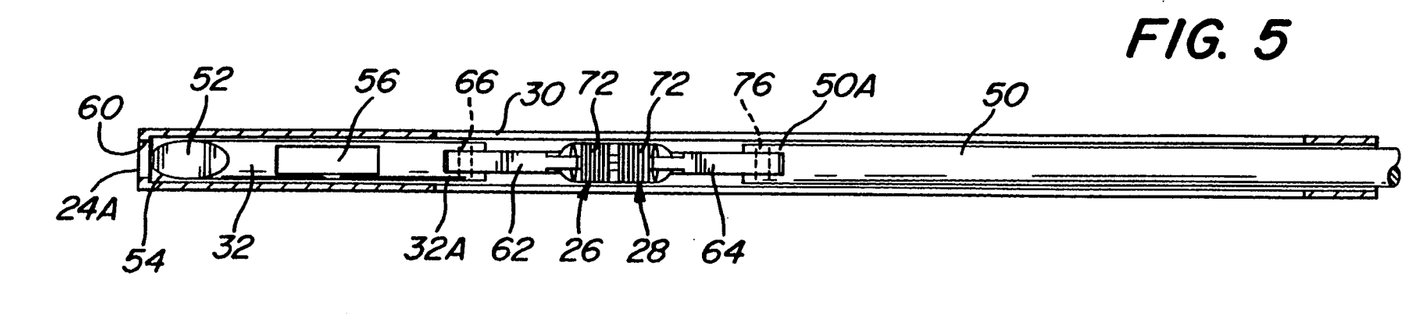
FIG. 5 is a longitudinal sectional view taken along line 5—5 of FIG. 4.

The details of the tip 32 can best be seen in FIGS. 1, 4 and 5. Thus, as can be seen therein, the tip 32 basically comprises a short rod-like element, whose outer diameter is just slightly less than the inner diameter of the sleeve 24. The rod-like element 32 has an angled flatted surface 52 at the distal end thereof. The interface of this surface with the periphery of the rod-like element 32 forms the heretofore mentioned sharp cutting edge 54.

A longitudinally extending slot 56 is provided in the rod-like element 32. This slot cooperates with a small projection 58 on the inner surface of the sleeve 24 located between the window 30 and the sleeve's open free end 24A to establish the limit of extension and retraction of the tip 32. To that end the projection 58 extends into the slot 56 and engages the proximal end of the slot to establish the limit of extension of the piercing tip 32 out of the sleeve. The engagement of the distal end of the slot 56 by the projection 58 establishes the limit of retraction of the tip within the sleeve.

As can be seen clearly in FIGS. 2, 4 and 5, a short height flange 60 is provided about the inner periphery of the open free end 24A of the sleeve 24. This flange serves as a stop to preclude the extension of the tip 32 out of the sleeve once it has been brought to its retracted position. In this regard when the tip 32 is retracted within the sleeve 24 to the retracted position its cutting edge 54 will pass beyond the inner edge of the flange 60, so that if the tip 32 is attempted to be extended out of the sleeve, as occurs when the jaws are operated (as will be described later), the cutting edge 54 engages and abuts the stop, whereupon further movement in the distal direction is precluded. This action effectively locks the tip's cutting edge 54 within the sleeve 24 and readies the instrument 20 to have its jaws 26 and 28 extended out of the window 30.

The means for effecting the extension/retraction of the jaws 26 and 28 with respect to the window 30 comprise a pair of support rods or links 62 and 64. The link 62 connects the jaw 26 to the piercing tip 32, while the link 64 connects the jaw 28 to the actuating rod 50. The jaws 26 and 28 are pivotally connected together.

The support link 62 is a short rod-like member having a diametrically oriented hole in the distal end thereof. The proximal end of the tip 32 is in the form of a yoke 32A (FIG. 5) having a diametrically oriented hole extending therethrough. The distal end of the support link 62 is located within the space formed by the yoke of the tip 32 so that the two holes are axially aligned. A pivot pin 66 is located within the aligned holes so that the support link 62 can be pivoted about that pin. The proximal end of the support link 62 includes a recess 68 its side through which a pivot pin 70 extends. The pivot pin 70 serves as the means for pivotally connecting the support link 62 to the jaw member 26. The jaw member 26 is an elongated member having a front face 72 including a multitude of small transverse serrations therein to form a good tissue grasping surface. The proximal end of the jaw member 26 is in the form of a hinge having a pivot pin 74 connecting it to the distal end of the jaw member 28.

The jaw member 28 is similar in construction to jaw member 26 and thus includes a serrated front face 72. The proximal end of the jaw member 28 includes a hole through which another pivot pin 70 extends. That other pivot pin 70 serves as the means for pivotally connecting the jaw member 28 to the support link 64. The support link 64 is similar in construction to the support link 62. Thus the other pivot pin 70 extends through a hole in the recess 68 at the distal end of the support link 64. The distal end of the actuating rod 50 includes a yoke 50A in which the proximal end of the support link 64 is located. The proximal end of the support link 64 includes an opening aligned with an opening in the yoke of the actuating rod and through which a pivot pin 76 extends to pivotally connect the support link 64 to the actuating rod 50.

The actuating rod 50 basically comprises an elongated cylindrical member which extends through the entire length of the sleeve 24 from the window 30 to the proximal end 24B (FIG. 1) of the sleeve. As can be seen in FIG. 1, the proximal end 24B of the sleeve extends through a longitudinal hole 78 in a front wall 80 the front of the housing body 22. The sleeve 24 is secured within that hole by any suitable means, e.g., an adhesive (not shown). The proximal end of the actuating rod 50 extends out of the proximal end 24B of the sleeve 24. The proximal end of the actuating rod includes the pin (previously mentioned) which is located within the slot 48 in the upper end of the trigger handle 36. Thus, pivoting of the trigger handle will be translated into reciprocating longitudinal motion of the actuating rod 50.

The operation of the instrument 20 will now be described with reference to FIGS. 1 and 4. As can be seen in FIG. 1, the instrument 20 is shown piercing through the epidermis 2, facia 4, muscle 6, and epithelium 8 over an insufflated abdominal cavity to grasp a portion, e.g., the left lobe 12 of the liver, to reflect it and thereby expose the gallbladder 14 so that some laparascopic procedure can be performed thereon via another instrument (not shown). To accomplish such tissue reflection the instrument 20 is initially configured so that its piercing tip 32 is in the extended position, i.e., the cutting edge 54 of the tip is extended beyond the free end 24A of the sleeve 24. The surgeon then grasps the instrument 20 in one hand, with his/her thumb being extended through the thumb hole 38 and his/her forefinger extended through the finger hole 40. The instrument is now ready to form the percutaneous incision or puncture into the patient's body. To that end the surgeon brings the tip's cutting edge into engagement with the patient's skin 2 located over the operative internal situs and pushes the instrument 20 inward. This action causes the sharp edge 54 to cut through the skin and the underlying tissue to form a small percutaneous incision or puncture 16. If necessary, or desired, some detent or biasing means (not shown) may be used in the instrument 20 to ensure that the piercing tip 32 does not slide rearward into the distal end of the sleeve during the tissue piercing operation.

Continued inward pushing on the instrument forces the distal portion of the sleeve 24 through the percutaneous puncture 16 until the distal end portion of the sleeve enters into the insufflated abdomen 10. This procedure can be monitored visually or electronically via any conventional means, e.g., a laparoscope.

Once the distal end portion of the instrument is within the insufflated abdomen the surgeon pushes his/her forefinger away from his/her thumb to pivot the trigger handle 36 away from the handle element 34 to the phantom line position shown in FIG. 1. This pivoting action overcomes the detent or biasing means, if used, and, in particular, causes the distal side of the slot 48 located in the upper end of the trigger handle 36 to engage the pin on the distal end of the actuating rod 50 to move the actuating rod through the sleeve 24 in the proximal direction, whereupon the piercing tip 32 is retracted until its cutting edge 54 is fully located within the distal end 24A of the sleeve. Accordingly, further manipulation or movement of the instrument 20 will not expose any adjacent integrally located tissue to injury from the sharp cutting edge 54.

With the piercing tip safely retracted the surgeon may then move and manipulate the instrument as desired until the sleeve's window 30 is located at the desired internal position, e.g., immediately adjacent and facing the left lobe 12 of the liver.

The instrument is now ready for extension of its jaws 26 and 28 out of the window 30 to grasp the tissue of the left lobe. To that end surgeon then pulls his/her forefinger towards his/her thumb to pivot the trigger handle 36 towards the handle 34 to the position shown in FIG. 3. This pivoting action causes the proximal side of the slot 48 to engage the pin on the proximal end of the actuating rod 50 to move the actuating rod in the distal direction, whereupon the piercing tip 32 is moved distally until its cutting edge 54 engages the inner surface of flange 60 at the opening 24B at the distal end of the sleeve. This action prevents the piercing tip from moving out of the sleeve. Continued squeezing of the trigger toward the handle element then causes the support link 64 to begin to pivot about its pin 76 in the clockwise direction as viewed in FIG. 4, while the support link 62 begins to pivot about its pin 66 in the counterclockwise direction. Since the support links 64 and 62 are pivotally connected to the jaws 28 and 28, respectively, the pivoting action of those links cause the jaws 28 and 26 to pivot toward each other about their hinge pin 74, whereupon the jaws extend outward through the window 30. When the jaws 26 and 28 are extended to the desired position, with the portion of the tissue to be grasped therebetween, further squeezing of the trigger handle 36 toward the handle element 34 causes to jaws to move together to clamp that tissue. The instrument can then be manipulated by the surgeon as desired, e.g., moved with respect to the percutaneous incision or puncture 16 through which the sleeve extends, to reflect the grasped tissue to some other internal position.

When the laparascopic procedure is finished and the surgeon wishes to release the grasped tissue and remove the instrument from the patient, all that needs to be done is to pivot the trigger handle 36 away from the handle element 34, in the same manner as describer earlier. This action causes the jaws to open, thereby releasing the tissue from therebetween. Continued pivoting of the trigger handle 36 away from the handle element 34 retracts the jaws and associated support links back through the window 30 fully into the sleeve 24.

The instrument can then be readily slid out of the percutaneous puncture 16. Since the puncture 16 is very small, once the instrument's sleeve 24 is removed the puncture immediately closes and hemostasis quickly ensues, Accordingly, suturing, stapling or other types of artificial sealing of the puncture 16 is not required.

In FIG. 7 there is shown the embodiment 200A of instrument of this invention. That instrument, like instrument 20, is arranged to pierce through the skin and underlying tissue of a patient to locate a pair of jaws at some internal situs to effect the grasping of tissue thereat. However, unlike the instrument 20, the instrument 200A includes jaws which are permanently oriented in the "extended" position. Notwithstanding that fact, the instrument 200A is still capable of forming and being extended through the same very small percutaneous incision or puncture 16 as formed by the instrument 20.

Thus, as can be seen in FIG. 7, the instrument 200A basically comprises housing or body portion 202 from which an elongated tubular sleeve assembly 204 extends. The sleeve assembly comprises an elongated sleeve 206, and an elongated rod or shaft 208 slidably mounted therein. The sleeve assembly 204 may be straight (as shown) or may be curved. In any case the distal end portion of the sleeve 206 includes an angularly oriented extension forming a jaw 210. In a similar manner the distal end portion of the shaft 208 includes an angularly oriented extension forming a jaw 212. The jaws are arranged to be slid with respect to each other parallel to the longitudinal axis 214 of the sleeve and rod so that then can be opened and closed. As pointed out earlier the use of the term "axis" in this application is not limited to a straight line, but can be a line of any shape, e.g., a curved line, since the sleeve assembly 204 need not be straight.

When the jaws 210 and 212 are completely closed, such as shown by the full lines in FIG. 7, they abut each other, whereupon the outer periphery of the conjoined jaws is substantially circular and of very small cross sectional area, e.g., the outside diameter of which is 0.109 inch (2.77 mm) or less. It is in this configuration that the instrument 200A is used to pierce through the patient's skin and underlying tissue to locate its jaws 210 and 212 within the body of the patient at the desired situs (as will be described later). Like the sleeve 22 of the instrument 20, the outside diameter of the sleeve assembly 204 is also very small, e.g., 0.109 inch (2.77 mm) or less, so that the formation of the percutaneous puncture 16 produced by the instrument 200A is very small and self-sealing.

The means for effecting the piercing operation of the instrument 200A comprises a piercing tip whose details will be described later. Suffice it for now to state that the piercing tip can take various embodiments, two of which, are shown herein. Those two embodiments of the piercing tip are merely exemplary and comprise a replaceable tip 300 of the instrument 200A and a pivotally extendable tip embodiment 400 of the instrument 200B. In either embodiment the piercing tip includes at least one cutting edge at its distal end for piercing skin and underlying tissue to effect the percutaneous insertion of the sleeve assembly of the instrument 200A or 200B into the patient's body.

The instruments 200A and 200B are similar in construction, except for their piercing tips. Thus, only instrument 200A will be described in detail hereinafter. To that end the body 202 of the instrument 200A basically comprises a hollow cylindrical housing 220 fixedly connected by a connector 222 to the proximal end of the sleeve 206. The housing 220 has a cylindrical interior cavity 226 in which a plunger assembly 228 is located. The plunger assembly is connected to the proximal end of the shaft 208 and serves as the means for sliding the shaft 208 within the sleeve 206 along axis 214 to effect the opening and closing of the jaws 210 and 212.

The plunger assembly 228 basically comprises a rod-like plunger element 230 having a distal end 232 at which the proximal end if the shaft 208 is fixedly secured. The outside diameter of the plunger element 230 is just slightly less than the inside diameter of the hollow interior 226 of the housing so that the plunger element can be slid longitudinally therethrough. The proximal end of the plunger element 230 is in the form of a cap or button 234 which extends through an opening 236 at the proximal end of the housing 220.

The housing 220 includes a pair of tabs 238 projecting perpendicular to the longitudinal axis 214 of the instrument 200A. A helical compression spring 240 is located within the hollow interior 226 of the housing 220 interposed between the distal end 232 of the plunger element 230 and an annular recess 224 in the inner surface of the connector 222. The spring 240 surrounds the proximal portion of the shaft 208 and serves to bias the plunger element 230 toward the full line, position shown in FIG. 7. In this orientation the jaws 210 and 212 of the instrument 200A are fully closed and, with the piercing tip 30 located thereon (as will be described later), the instrument arranged to form the percutaneous incision or puncture 16.

In order to center the shaft 208 within the sleeve 206 and to facilitate its sliding action within the sleeve 206, a linear bushing 242 is located within a second annual recess 244 in the connector 222.

As can be seen in FIG. 7, the jaw 210 comprises an angular extension of the distal end of the sleeve 206. The angular extension is slightly thicker than the thickness of the sleeve's sidewall and includes an inner surface 246 having a plurality of transversely extending serrations to form a good tissue grabbing surface (like the surface 72 described with reference to instrument 20). The jaw 212 comprises an extension of the shaft 208 and also includes a serrated inner surface 246.

The cross sectional profile of each of the jaws taken perpendicularly to their longitudinal axis 248 is generally hemispherical so that when the jaws are fully closed, i.e., when their serrated inner surfaces abut, the profile of the conjoined jaws 210 and 212 is circular and of very small cross sectional area, e.g., the outside diameter of which is 0.109 inch (2.77 mm) or less.

A recess 250 is provided in the outer periphery of each of the jaws 210 and 212 very close to the distal end thereof These recesses merge when the jaws 210 and 212 are fully closed to form an annular groove extending about the periphery of the conjoined jaws. The annular groove serves as the means for releasably securing the piercing tip 300 thereon.

The piercing tip 300 basically comprises a member having a pyramidally shaped distal end 302 and a hollow proximal end 304. The hollow proximal end includes a cavity 306 formed by a peripheral sidewall of the tip. The lip of the sidewall has an inwardly directed bead 308 extending about the inner periphery thereof. The cavity 306 is arranged to accommodate the distal end of the instrument's closed jaws so that the bead 308 snap-fits into the annular groove formed by the recess 250 to releasably secure the piercing tip 300 onto the instrument 200A. The pyramidal end 302 of the piercing tip 300 includes four cutting edges 310 which merge together at the apex of the tip.

The operation of the instrument 200A using the tip 300 to effect tissue reflection like that described earlier with respect to instrument 20 will now be described. To accomplish that operation the piercing tip 300 is mounted on the distal end the instrument 200A as described above so that its cutting edges 310 are exposed. The surgeon then grasps the instrument 200A in one hand, with his/her thumb being disposed on the cap 234 and with his/her forefinger and index finger disposed on the respective extending tabs 238. The instrument 200A is now ready to form the percutaneous incision or puncture 16 into the patient's body. To that end the surgeon brings the tip 300 into engagement with the patient's skin located over the operative internal situs, e.g., the insufflated abdomen 10, and orients the instrument so that the conjoined angularly extending jaws are oriented in the desired direction, e.g., perpendicularly, with respect to the patient's body and then pushes that portion of the instrument inward. This action causes the sharp cutting edges 310 of the tip to cut through the skin and the underlying tissue to form a small percutaneous incision or puncture 16.

Once the conjoined angularly extending jaws are within the insufflated abdomen 10 the instrument is then oriented as shown in FIG. 6 so the contiguous, longitudinally extending portion of the sleeve assembly 204 passes through the percutaneous incision or puncture 16. Continued inward pushing on the instrument forces more of the sleeve assembly through the puncture 16 until the jaws are at the desired internal position. This procedure can be monitored visually or electronically via any conventional means, e.g., a laparoscope.

The surgeon may then remove the tip 30 from the instrument 200A via some means (not shown) inserted into the patient's abdomen through another very small percutaneous incision or puncture. The removed tip 300 may be extracted from the body of the patient through that other percutaneous incision. or puncture. If the tip is formed of a resorbable material, e.g., polyglycolide, etc., it may be left in the body after it has been removed from the conjoined jaws 210 and 212.

In any event once the tip 300 has been removed the jaws 210 and 212 are freed so that instrument 200A is ready to be used to grasp adjacent tissue. To that end the surgeon applies thumb and finger pressure to the thumb cap 234 and finger tabs 238, respectively, to move the plunger element 230 further into the housing to the phantom line position shown in FIG. 7. The movement of the plunger causes the concomitant movement of the shaft 208 within the sleeve 206 against the bias force produced by the compression spring 240. This action has the effect of moving the jaw 212 away from the jaw 210, thereby opening the jaws, whereupon internal tissue can be located therebetween.

Figure 8:
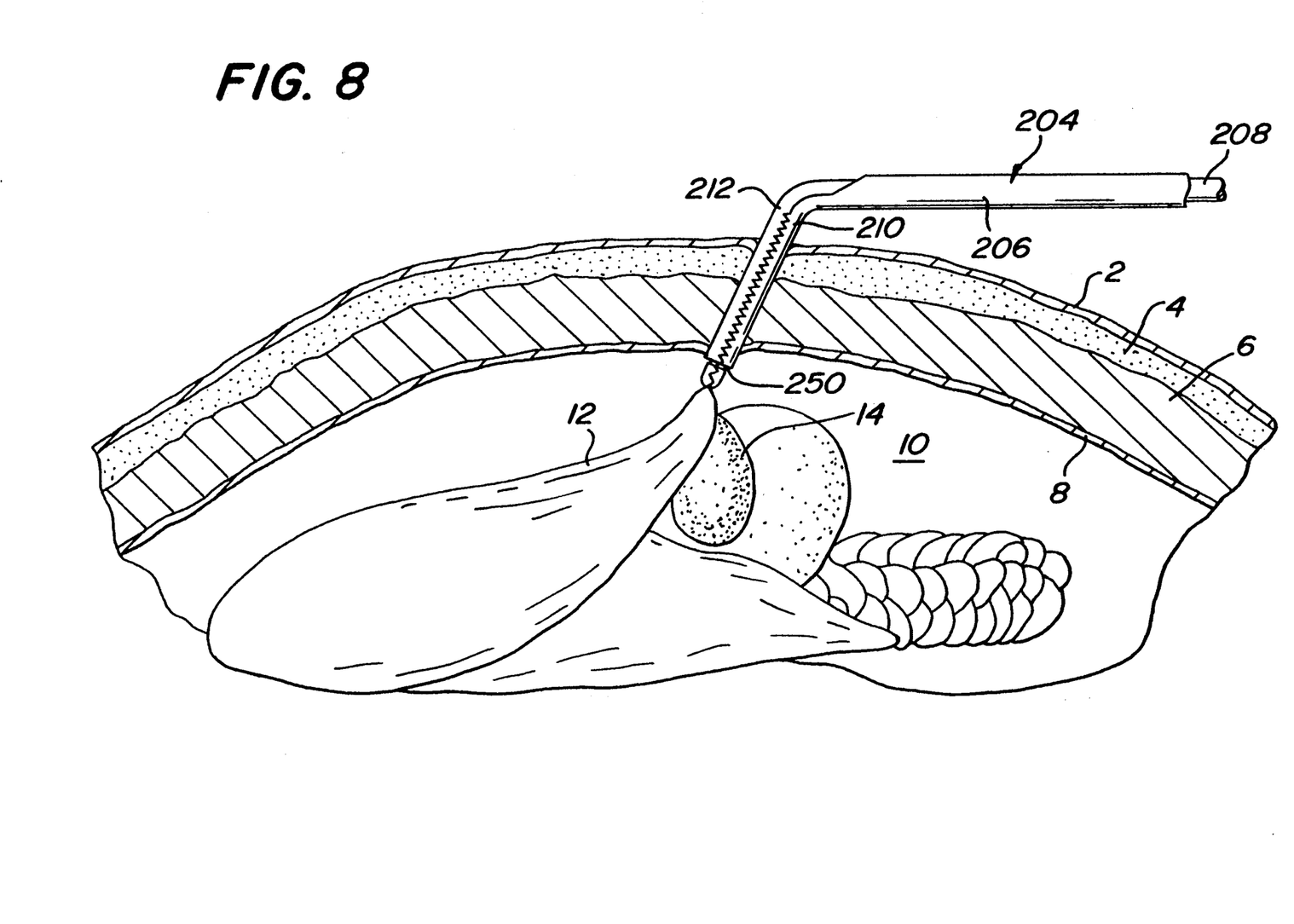
FIG. 8 is a side elevational view, partially in section, showing the second preferred embodiment of the instrument after its piercing tip has been removed and with its jaws grasping and reflecting internal tissue.

In order to grasp that tissue the surgeon merely has to release the thumb pressure on the cap, whereupon the spring 240 carries the plunger element and the shaft 208 in the proximal direction until the jaws close on the interposed tissue. That tissue can then be held in position or reflected, as shown in FIG. 8, depending upon the desires of the surgeon. Once the laparoscopic procedure has been accomplished, the surgeon may release the grasped tissue by again applying thumb pressure on the thumbcap 234 while his/her fingers hold the tabs 238. After the tissue is released the instrument 200A can be readily slid out of the percutaneous incision or puncture 16, so that the incision or puncture immediately closes and seals itself.

Attention will now be directed to FIG. 9 wherein the details of the extendable piercing tip 400 of instrument 200B are shown. The tip 400 is permanently mounted on the distal end of the jaw 212. The tip 400 basically comprises a member having a planar surface forming a sharp cutting edge 402 at one end thereof and an arcuate surface 404 at the other end. The tip is located within a longitudinally extending slot 406 in the jaw 212. A pivot pin 408 extends through a pair of aligned holes 410 in the sidewalls forming the slot 406. The pin 408 extends through a hole 412 extending transversely through the tip 400. A helical spring 414 is disposed within the hole 412 and about the pivot pin 408. The spring 414 serves to bias the tip 400 to the retracted position shown in FIG. 10, wherein the tip's cutting edge 402 is located within the slot 406. To accomplish that action one end 416 of the spring engages a portion of the jaw 212 immediately adjacent the slot 406 while the other end 418 of. the spring 414 engages a portion of the interior of the tip 400.

In order to extend the tip 400 from its retracted position shown in FIG. 10 to the extended position shown in FIG. 9, so that the instrument 200B can be used to pierce through the patient's skin and underlying tissue, the tip is pivoted against the bias of the spring about the pin 408 to bring its tip into axial alignment with the angularly extending jaw 212. The distal end of a stop rod 420 extending longitudinally through a passageway 422 in the jaw 212 is positioned to engage the arcuate surface 404 of the cutting tip 400 as shown in FIG. 9. This holds the tip 400 in the extended position against the bias of the spring 414.

The instrument 200B may then be used to form the percutaneous puncture 16 in the same manner as described with respect to instrument 200A. When the distal end of the instrument 400B is within the insufflated abdomen, an actuator (not shown) forming a part of the instrument 200B and coupled to the stop rod 420 is operated by the surgeon to retract the stop rod away from tip 400. This action enables the spring 414 to rotate the tip 400 in the clockwise direction shown in FIG. 10 so that its cutting edge 402 enters within the slot 406. The stop rod 420 can then be extended slightly distally to overlie the tip's cutting edge as shown in FIG. 10, thereby insuring that the cutting tip is locked in the retracted position within the slot in jaw 212. The instrument 200B can then be used as described with reference to the instrument 200A.

Without further elaboration the foregoing will so fully illustrate our invention that others may, by applying current or future knowledge, adopt the same for use under various conditions of service.

What is claimed is:

1. An apparatus for performing some medical procedure in the body of a being, said apparatus having a proximal portion, an intermediate portion, and a distal portion, said proximal portion being arranged to be located outside the body of said being, said distal portion and a portion of said intermediate portion being arranged to be located within an interior portion of the body of said being, said intermediate portion being elongated and having a longitudinal axis, said distal portion comprising piercing means and at least two working means, each of said working means extending laterally of said longitudinal axis prior to the introduction thereof into the body of said being, and with at least one of said working means being actuatable, said piercing means being coupled to at least one of said working means for commencing the formation of a small percutaneous incision or puncture in the body of said being, whereupon said distal portion of said apparatus can be inserted through said incision or puncture into the body of said being to a desired internal position without the use of a trocar or other introducing means, said piercing means being sufficiently sharp to form at least a portion of said incision or puncture and being movable to a safety state when said distal portion is within said interior portion, whereupon said piercing means does not pose any hazard to interior tissue, said incision or puncture formed by said piercing means being sufficiently small that it is quickly self-sealing after said distal portion of said apparatus has been removed therefrom, at least one of said working means being movable with respect to the other of said working means for engagement with tissue located adjacent said internal position to perform some operation thereon when said at least one actuatable means is actuated.

2. The apparatus of claim 1 wherein said proximal portion of said apparatus is arranged to be located outside the body of said being while said distal portion is located therein, said proximal portion of said apparatus comprising actuating means for actuating said first actuatable means.

3. The apparatus of claim 1 wherein said distal portion of said apparatus comprises a first end portion and wherein said piercing means comprises a piercing tip, said piercing tip being movable with respect to said first end portion to convert said piercing means to said safety state.

4. The apparatus of claim 3 wherein said piercing tip is releasably secured to said first end portion, whereupon said piercing tip may be removed therefrom after said piercing tip has formed said small percutaneous incision or puncture.

5. The apparatus of claim 4 wherein said proximal portion of said apparatus is arranged to be located outside the body of said being while said distal portion is located therein, said proximal portion of said apparatus including actuating means for actuating said first actuatable means.

6. The apparatus of claim 3 wherein said proximal portion of said apparatus is arranged to be located outside the body of said being while said distal portion is located therein, said proximal portion of said apparatus including actuating means for actuating said first actuatable means.

7. An apparatus for performing some medical procedure in the body of a being, said apparatus having a proximal portion, an intermediate portion, and a distal portion, said proximal portion being arranged to be located outside the body of said being, said distal portion and a portion of said intermediate portion being arranged to be located within the body of said being, said intermediate portion being elongated and having a longitudinal axis, said distal portion comprising piercing means and at least two jaws extending laterally of said longitudinal axis prior to the introduction thereof into the body of said being, with at least one of said jaws being actuatable, said piercing means being coupled to at least one of said jaws for commencing the formation of a small percutaneous incision or puncture in the body of said being, whereupon said distal portion of said apparatus can be inserted through said incision or puncture into the body of said being to a desire internal position without the use of a trocar or other introducing means, said incision or puncture formed by said piercing means being sufficiently small that it is quickly self-sealing after said distal portion of said apparatus has been removed therefrom, said jaws being arranged to move relative to each other in directions generally parallel to said longitudinal axis for engagement with tissue located adjacent said internal position to perform some operation thereon when at least one of said jaws is actuated 8. The apparatus of claim 7 wherein said proximal portion of said apparatus is arranged to be located outside the body of said being while said distal portion is located therein, said proximal portion of said apparatus including actuating means for actuating said first actuatable means.

9. The apparatus of claim 7 wherein said piercing means comprises a piercing tip, said piercing tip forming a portion of at least one of said jaws.

10. The apparatus of claim 9 wherein said piercing tip being movable with respect to said first end portion to enable said piercing tip to be moved to a safety position after said piercing tip has formed said small percutaneous incision or puncture.

11. The apparatus of claim 10 wherein said piercing tip is releasably secured to one jaw, whereupon said piercing tip may be removed therefrom after said piercing tip has formed said small percutaneous incision or puncture.

12. The apparatus of claim 11 wherein said proximal portion of said apparatus is arranged to be located outside the body of said being while said distal portion is located therein, said proximal portion of said apparatus including actuating means for actuating said first actuatable means.

13. The apparatus of claim 10 wherein said proximal portion of said apparatus is arranged to be located outside the body of said being while said distal portion is located therein, said proximal portion of said apparatus including actuating means for actuating said first actuatable means.

14. A method for performing a medical procedure at a predetermined internal position within the body of a being by the use of an apparatus having proximal portion, an intermediate portion having a longitudinal axis, and a distal portion, said distal portion comprising at least two working means, at least one of which is actuatable, and substantially sharp piercing means, said working means projecting outward laterally of said longitudinal axis of said intermediate portion, said method comprising the steps of locating said piercing means adjacent at least one of said working means, orienting said distal portion of said apparatus so that it is at desired orientation with respect to the skin of the being located over said internal position, bringing said piercing means into engagement with the body of said being to start the formation of a small percutaneous incision or puncture in the body of said being, and thereafter moving said distal portion of apparatus in to the started incision or puncture so that said distal portion of said apparatus extends therethrough and through the tissue underlying the skin, whereupon said incision or puncture is completed and said working means is located at said internal position without using a trocar or any other introducing means, moving said piercing means to a safety state by the time that said working means is located at sad internal position, whereupon said piercing means does not present any hazard to tissue located at said internal position, locating said proximal portion of said apparatus outside the body of said being when said distal portion is located at said internal position, and actuating said at least one actuatable working means from said proximal portion to cause said at least one of said working means to move with respect to the other of said working means so that at least one of said working means engages tissue located at said internal position to perform some operation on said tissue, said percutaneous incision or puncture formed by said piercing means being sufficiently small that it will quickly seal itself once said distal portion of said apparatus has been removed therefrom.

15. The method of claim 14 wherein said distal portion of said apparatus comprises a first end portion and wherein said piercing means comprises a piercing tip, said method comprising moving said piercing tip with respect to said first end portion to convert said piercing means to said safety state after said piercing tip has formed said small percutaneous incision or puncture.

16. The method of claim 15 comprising releasably securing said piercing tip to said first end portion during the formation of said incision or puncture, and removing said piercing tip from said first end portion after piercing tip has formed said incision or puncture so that said piercing means is converted to said safety state.

17. A method for performing a medical procedure at a predetermined internal position within the body of a being by the use of an apparatus having proximal portion, an intermediate portion having a longitudinal axis, and a distal portion, said distal portion comprising at least two working means, at least one of which is actuatable, and substantially sharp piercing means, said working means projecting outward laterally of said longitudinal axis of said intermediate portion and comprising a pair of jaws which are arranged to be moved relative to each other in directions generally parallel to said longitudinal axis, said method comprising the steps of locating said piercing means adjacent at least one of said jaws, orienting jaws so that they are at a desired orientation with respect to the skin of the being located over said internal position, bringing said piercing means into engagement with the body of said being to start the formation of a small percutaneous incision or puncture in the body of said being, and thereafter moving said jaws of said apparatus into the started incision or puncture so that said distal portion of said apparatus extends therethrough and through the tissue underlying the skin, whereupon said incision or puncture is completed and said jaws are located at said internal position without using a trocar or any other introducing means, converting said piercing means to a safety state by the time that said jaws are located at said internal position, whereupon said piercing means does not present any hazard to tissue located at said internal position, locating said proximal portion of said apparatus outside the body of said being when said distal portion is located at said internal position, and operating said proximal portion of said apparatus to move at least one of said jaws relative to the other after said distal portion of said apparatus has been inserted into the body of said being at said internal position.

18. The method of claim 17 wherein said jaws are moved together to grasp internally located tissue therebetween.

19. The method of claim 18 additionally comprising the step of manipulating said apparatus by said proximal portion to effect the positioning of said tissue.

20. The method of claim 17 wherein said jaws are moved together to grasp internally located tissue therebetween.

21. The method of claim 20 additionally comprising the step of manipulating said apparatus by said proximal portion to effect the positioning of said tissue.

22. An instrument for performing some medical procedure in an interior portion of the body of a living being from outside the body of said being via a small percutaneous incision or puncture, said instrument having a proximal portion, a distal portion, working means, and tissue penetration means, said distal portion being elongated, said working means being mounted on said distal portion, said proximal portion being arranged to be held outside the body of said being, said distal portion additionally comprising tissue penetration means including movable piercing member, said piercing member being movably coupled to said distal portion and arranged to be in an exposed position to pierce through a portion of the skin of said being, said tissue penetration means being arranged to pass through said pierced portion of skin and through tissue underlying said portion of skin to form said percutaneous incision or puncture upon the application of force to said instrument, whereupon said distal portion and said working means passes through said incision or puncture into said interior portion without the use of a trocar or other introducing means and so that said working means is located at a desired position within said interior portion, said piercing member being movable from said extended position to a safety position, whereupon said piercing member does not present any hazard to tissue located at said interior portion, said working means being movable with respect to said distal portion of said instrument within the said interior portion to perform a predetermined function therein under control of first means located outside the body of said being.

23. The instrument of claim 22 wherein said first means comprise actuating means located at said proximal portion of said instrument.

24. The instrument of claim 23 additionally comprising mechanical coupling means coupled between said actuating means and said working means.

25. The instrument of claim 24 wherein said working means comprises a pair of jaws for grasping tissue therebetween.

26. The instrument of claim 22 wherein said working means comprises a pair of jaws for grasping tissue therebetween.

* * * * *